US00PP31191P2

(12) United States Plant Patent
Bradford et al.

(10) Patent No.: US PP31,191 P2
(45) Date of Patent: Dec. 10, 2019

(54) PLUM TREE NAMED 'PLUMCANDY XV'

(50) Latin Name: *Prunus salicina*
Varietal Denomination: Plumcandy XV

(71) Applicants: Lowell Glen Bradford, Le Grand, CA (US); Jon M. Quisenberry, Le Grand, CA (US)

(72) Inventors: Lowell Glen Bradford, Le Grand, CA (US); Jon M. Quisenberry, Le Grand, CA (US)

( * ) Notice: Subject to any disclaimer, the term of this patent is extended or adjusted under 35 U.S.C. 154(b) by 0 days.

(21) Appl. No.: 16/350,704

(22) Filed: Dec. 26, 2018

(51) Int. Cl.
*A01H 5/08* (2018.01)
*A01H 6/74* (2018.01)

(52) U.S. Cl.
USPC ..... Plt./184
CPC ..... *A01H 6/74* (2018.05)

(58) Field of Classification Search
USPC ..... Plt./184
CPC ..... A01H 5/0862
See application file for complete search history.

(56) References Cited

U.S. PATENT DOCUMENTS

PP14,220 P2 10/2003 Bradford
PP16,369 P2 3/2006 Bradford

*Primary Examiner* — Kent L Bell

(57) ABSTRACT

The present invention relates to a plum tree and more particularly to a new and distinct variety broadly characterized by a medium size, vigorous, hardy, and productive tree. Being self-unfruitful, the present variety requires cross pollination from another plum or interspecific tree that blooms during the mid to late season, such as 'Plumsweet X' interspecific tree (U.S. Plant Pat. No. 19,528). The present variety's abundance of blossoms and moderate pollen production entices strong bee activity to facilitate pollination. The fruit matures under the ecological conditions described during the second week of September, with first picking on Sep. 13, 2018. The fruit is uniform, medium in size, almost full red in skin color, clingstone in type, red to pink in flesh color, firm in texture, juicy, very sweet and excellent in flavor.

1 Drawing Sheet

Botanical classification: *Prunus salicina.*
Variety denomination: 'PLUMCANDY XV'.

BACKGROUND OF THE VARIETY

In a continuing effort to improve the quality of shipping fruits, we, the inventors, typically hybridize a large number of peach, nectarine, plum, apricot, and cherry seedlings each year. We also grow a lesser number of open pollinated seeds of each of these fruits. The present invention relates to a new and distinct variety of plum tree, which has been denominated varietally as 'Plumcandy XV'.

During a typical blooming season we isolate as seed parents both individual and groups of different plum and interspecific trees by covering them with screen houses. A hive of bees is placed inside each such house, and bouquets to provide pollen from different plum, apricot, and interspecific hybrid trees are placed in buckets near the trees approximately every two days for the duration of the bloom. During 2007 one such house containing 'September Yummy®' plum tree (U.S. Plant Pat. No. 14,220) was crossed by us in this manner. To pollinate this plum tree, we selected bouquets from several sources of other plum and interspecific trees without keeping specific written details. Upon reaching maturity the fruit from this plum tree was harvested, and the seeds were removed, cracked, stratified and germinated as a group with the label "H16". They were grown as seedlings on their own root in our greenhouse and upon reaching dormancy transplanted to a cultivated area of our experimental orchard located near Le Grand, Calif. in Merced County (San Joaquin Valley). During the summer of 2011 the claimed variety was selected by us as a single plant from the group of seedlings described above. Subsequent to origination of the present variety of plum tree, we asexually reproduced it by budding and grafting in the experimental orchard described above, and such reproduction of plant and fruit characteristics were true to the original tree in all respects. The reproduction of the variety included the use of 'Nemaguard' (unpatented) rootstock upon which the present variety was compatible and true to type.

The present variety is similar to its seed parent, 'September Yummy®' (U.S. Plant Pat. No. 14,220) plum tree, by blooming in the mid season, by being self-unfruitful, and by producing fruit that is nearly full red in skin color, sweet, juicy, firm, and very good in flavor, but is distinguished therefrom by producing fruit that is smaller in size, that is red instead of yellow in flesh color, that is clingstone intead of semi-freestone in type, and that ripens about fifteen days earlier.

The present variety is most similar to 'Plumsweet V' (U.S. Plant Pat. No. 16,369) interspecific tree, by having a medium size tree, by being self-unfruitful, by blooming in the mid season, by being productive, and by producing fruit that has mostly red skin with freckles, that is medium in size, that is firm in texture, that is clingstone in type, and that is sweet in flavor, but is distinguished therefrom by producing fruit that is red instead of yellow in flesh color, that is heart shaped instead of oblate, and that matures about eighteen days later.

SUMMARY OF VARIETY

The present plum variety is characterized by a medium size, vigorous, hardy, and productive tree. Being self-unfruitful, the present variety requires cross pollination from another plum or interspecific tree that blooms during the mid to late season, such as 'Plumsweet X' interspecific tree (U.S. Plant Pat. No. 19,528). The present variety's abundance of blossoms and moderate pollen production entices strong bee activity to facilitate pollination. The fruit matures under the ecological conditions described during the second week of September, with first picking on Sep. 13, 2018. The fruit is uniform, medium in size, almost full red in skin color, clingstone in type, red to pink in flesh color, firm in texture, juicy, very sweet and excellent in flavor.

DRAWING

The accompanying photograph exhibits four whole fruits positioned to display the characteristics of the skin color and form, one divided fruit to reveal the flesh and stone, typical leaves, and two insets depicting the flower buds and blossoms as they appeared on the tree during the blooming season.

POMOLOGICAL CHARACTERISTICS

Referring now more specifically to the pomological characteristics of this new and distinct variety of plum tree, the following has been observed under the ecological conditions prevailing near Le Grand, Merced County (San Joaquin Valley), Calif., and was developed at the state of shipping ripe on Sep. 13, 2018, on the original tree during its eleventh growing season. All major color code designations are by reference to the Inter-Society Color Council, National Bureau of Standards. Common color names are also used occasionally.

PARENTAGE

Seed parent: 'September Yummy®' (U.S. Plant Pat. No. 14,220) plum tree.
Pollen parent: Unknown.

TREE

Size: Medium, reaching and maintaining a height of 8' [2.44 m.] and a spread of 9' [2.74 m.] after eleven growing seasons utilizing typical dormant pruning.
Vigor: Vigorous, responding typically to irrigation and fertilization. The variety grows about 3' [0.91 m.] of surplus top-growth during the spring and summer. The plant should be grown on a standard commercial rootstock for production purposes.
Growth: Spreading and dense.
Form: Pruned to a vase formed type.
Hardiness: Hardy with respect to central California winters.
Heat tolerance: Observed to perform adequately in typical central California climatic conditions, which typically include prolonged periods of heat.
Drought tolerance: Variety is developed for commercial orchards and requires regular irrigation.
Production: Productive, thinning usually necessary.
Fertility: Self-unfruitful, requiring cross pollination by a suitable mid seasonal blooming plum or interspecific, such as 'Plumsweet X' interspecific tree (U.S. Plant Pat. No. 19,528).
Bearing: Fairly regular, weather dependent, no crop failures observed as of yet.
Leaf bud burst: Late, toward the end of flowering.

Trunk:
*Size*.—Medium, reaching a maximum diameter of 5" [127 mm.] after eleven growing seasons.
*Texture*.—Medium, shaggy.
*Bark color*.—A Moderate brown [58. m.Br] and Moderate yellowish brown [77. m.yBr] variegation with Deep yellowish brown [75. deep yBr] crevices present.
*Lenticels*.—Approximate Number Per Square Inch: 8. Color: Strong brown [55. s.Br]. Typical Size: ¼" [6.4 mm.] in length. The width is typically one fourth as much as the length. Shape: Eye-shaped.

Branches:
*Size*.—Diameter of the scaffold is 2½" [63.5 mm.] measured 12" above the crotch, limb diameter is 1" [25.4 mm.] measured 12" above the first fork.
*Texture*.—Smooth on first year wood, increasing roughness with age.
*Color*.—1st Year Wood Topside: Grayish red [19. gy.R]. 1st Year Wood Underside: Brilliant yellow green [116. brill.YG]. 2nd Year Wood: A Grayish brown [61. gy.Br] and Grayish yellowish brown [80. gy.yBr] variegation.
Lenticels.—Approximate Number Per Square Inch: 24. Color: Light yellowish brown [76. l.yBr]. Typical Size: 1/32" [0.8 mm.] in length. The width is typically one fourth as much as the length. Shape: Eye-shaped.

Leaves:
*Size*.—Medium to large. Average Length: 5⅛" [130.2 mm.]. Average Width: 2⅜" [60.3 mm.].
*Arrangement*.—Alternate.
*Thickness*.—Medium.
*Form*.—Elliptical.
*Apex*.—Acuminate.
*Base*.—Acute with an average base angle of seventy-five degrees.
*Surface*.—Smooth on both sides.
*Color*.—Dorsal Surface: Moderate olive green [125. m.OlG]. Ventral Surface: Moderate yellow green [120. m.YG].
*Red midvein*.—Absent.
*Margin*.—Finely serrate.
*Venation*.—Pinnately net veined.
*Petiole*.—Average Length: ⅝" [15.9 mm.]. Average Thickness: 1/16" [1.6 mm.]. Color: Moderate greenish yellow [102. m.gY].
*Stipules*.—Number: 2 per leaf, up to 6 per growing tip. Average Length: ¼" [6.4 mm.]. Color: Strong yellow green [117. s.YG] becoming Dark olive [108. d.Ol] with age.
*Glands*.—Number: 2. Position: Usually alternate, positioned at the intersection of the petiole and base blade. Form: Globose. Size: Medium, 1/32" [0.8 mm.] in diameter. Color: Moderate yellow green [120. m.YG] becoming Dark brown [59. d.Br] with age.
*Leaf buds*.—Pointed.

Flower buds:
*Hardiness*.—Hardy, with respect to the central California blooming season.
*Diameter*.—Typically 3/16" [4.8 mm.] 1 week before bloom.
*Length*.—Typically 5/16" [7.9 mm.] 1 week before bloom.

*Form*.—Not appressed.
*Surface*.—Slightly pubescent.
*Color*.—White [263. White].

Flowers: Perfect, complete, usually a single pistil, about twenty-four stamens, five sepals and petal locations alternately positioned.
*Average flower diameter*.—15/16" [23.8 mm.].
*Average flower depth*.—1/4" [6.4 mm.] when fully open.
*Average pedicel length*.—1/4" [6.4 mm.].
*Number of petals*.—Five, no double blossoms observed.
*Petal arrangement*.—Overlapping.
*Petal shape*.—Oval to slightly ovate.
*Petal margin*.—Entire, wavy.
*Average petal diameter*.—5/16" [7.9 mm.].
*Average petal length*.—7/16" [11.1 mm.].
*Petal apex*.—Rounded to slightly ovate.
*Petal base*.—Rounded to slightly cuneate.
*Petal color*.—White [263. White] on both sides.
*Anther color*.—Pale yellow [89. p.Y].
*Pollen production*.—Medium.
*Pollen color*.—Light yellow [86. l.Y].
*Stigma color*.—Light greenish yellow [101. l.gY].
*Stigma position*.—Stigma is located about 1/8" [3.2 mm.] below the average anther position.
*Ovary*.—Non-pubescent.
*Sepal color*.—Light yellow green [119. l.YG] on both sides.
*Sepal length*.—5/32" [4.0 mm.].
*Sepal width*.—1/8" [3.2 mm.].
*Sepal apex*.—Elliptical to match the width and length.
*Average pistil length*.—7/16" [11.1 mm.].
*Average stamen length*.—5/16" [7.9 mm.].
*Stamen position*.—Typically located about 1/16" [1.6 mm.] above the petals.
*Ovary*.—Smooth.
*Fragrance*.—Moderate.
*Blooming period*.—Medium compared with other varieties, about six days ahead of 'September Yummy®' plum (U.S. Plant Pat. No. 14,220).
*Onset of bloom*.—One percent on Feb. 24, 2018.
*Date of full bloom*.—Mar. 3, 2018.
*Duration of bloom*.—One to two weeks, dependent on ambient temperature.
*Bloom density*.—Heavy.
*Number per cluster*.—Typically 2 or 3, up to 9 observed.

FRUIT

Maturity when described: Shipping ripe, Sep. 13, 2018.
Date of first picking: Sep. 13, 2018.
Date of last picking: Sep. 30, 2018.
Size: Uniform, medium.
*Average diameter axially*.—2 5/8" [66.7 mm.].
*Average diameter across suture plane*.—2 1/2" [63.5 mm.].
*Average diameter across cheek plain*.—2 1/2" [63.5 mm.].
*Typical weight*.—4.9 ounces [139 grams].
Form: Fairly uniform, mostly symmetrical, slightly elongated, heart shaped.
*Longitudinal section form*.—Round.
*Transverse section through diameter*.—Heart shaped.
Suture: A distinct Pale yellow [89. p.Y] line located in a shallow trough extending from the base to the apex.
Ventral surface: Rounded.
Lips: Somewhat unequal.
Cavity: Flaring.
*Depth*.—1/2" [12.7 mm.].
*Breadth*.—7/8" [22.2 mm.].
*Stem markings*.—Usually not present.
Base: Truncate, moderately cordate when viewed parallel to the suture.
Apex: Rounded.
Pistil point: An inconspicuous Pale yellow [89. p.Y] dot.
Stem: Medium size.
*Average length*.—3/8" [9.5 mm.].
*Average width*.—1/16" [1.6 mm.].
Skin:
*Thickness*.—Medium.
*Surface*.—Smooth.
*Tenacity*.—Tenacious to flesh.
*Astringency*.—Moderate.
*Tendency to crack*.—None observed.
*Color*.—Very deep red [14. v.deep R] over a Moderate red [15. m.R] background with heavy Pale yellow [89. p.Y] freckling throughout.
*Lenticels*.—Number Per Square Inch: About 120. Average diameter: 1/96" [0.26 mm].
*Bloom*.—Heavy.
Flesh:
*Color*.—Deep red [13. deep R] near the skin smoothly blending to Deep pink [3. deep Pk] toward the stone with Light yellowish pink [28. l.yPk] fibers throughout.
*Surface of pit cavity*.—Covered with Deep yellowish pink [27. deep yPk] broken fibers when twisted away from stone.
*Amygdalin*.—Moderate.
*Juice*.—Moderate.
*Texture*.—Firm, crisp.
*Fibers*.—Abundant, fine, tender.
*Ripens*.—Fairly even, earliest at the shoulder.
*Flavor*.—A tasty blend of acid and sugar, typically 21 brix.
*Aroma*.—Very slight.
*Eating quality*.—Excellent.

STONE

Type: Clingstone.
Form: Obovate to round.
Hilum: Narrow.
Base: Rounded.
Apex: Acute with a short tip 1/16" [1.6 mm.] in length.
Sides: Fairly equal.
Surface: Rough.
External color of stone: Dark orange yellow [72. d.OY].
Pit wall color when cracked: Pale orange yellow [73. p.OY].
Cavity surface color: Strong brown [55. s.Br].
Average pit wall thickness: 1/8" [3.2 mm.].
Average length: 1 1/16" [27.0 mm.].
Average width: 3/4" [19.1 mm.].
Average breadth: 7/16" [11.1 mm.].
Tendency to split: None observed.
Kernel:
*Form*.—Oval.
*Pellicle color*.—Pale orange yellow [73. p.OY].

*Skin color*.—Strong yellowish brown [74. s.yBr].
*Vein color*.—Deep yellowish brown [75. deep yBr].
*Taste*.—Bitter.
*Viable*.—Yes.
*Average length*.—⅝" [15.9 mm.].
*Average width*.—⅜" [9.5 mm.].

USE

Market: Fresh market and long distance shipping.
Keeping quality: Excellent. Fruit quality observed to remain in good condition after 30 days in standard cold room at 36° Fahrenheit [2° Celsius].
Shipping quality: Excellent.
Resistance to insects: Not tested.
Resistance to diseases: Not tested.

OTHER NOTES

Although the new variety of plum tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of plum tree, *prunus salicina*, substantially as illustrated and described, that is most similar to 'Plumsweet V' (U.S. Plant Pat. No. 16,369) interspecific tree, by having a medium size tree, by being self-unfruitful, by blooming in the mid season, by being productive, and by producing fruit that has mostly red skin with freckles, that is medium in size, that is firm in texture, that is clingstone in type, and that is sweet in flavor, but is distinguished therefrom by producing fruit that is red instead of yellow in flesh color, that is heart shaped instead of oblate, and that matures about eighteen days later.

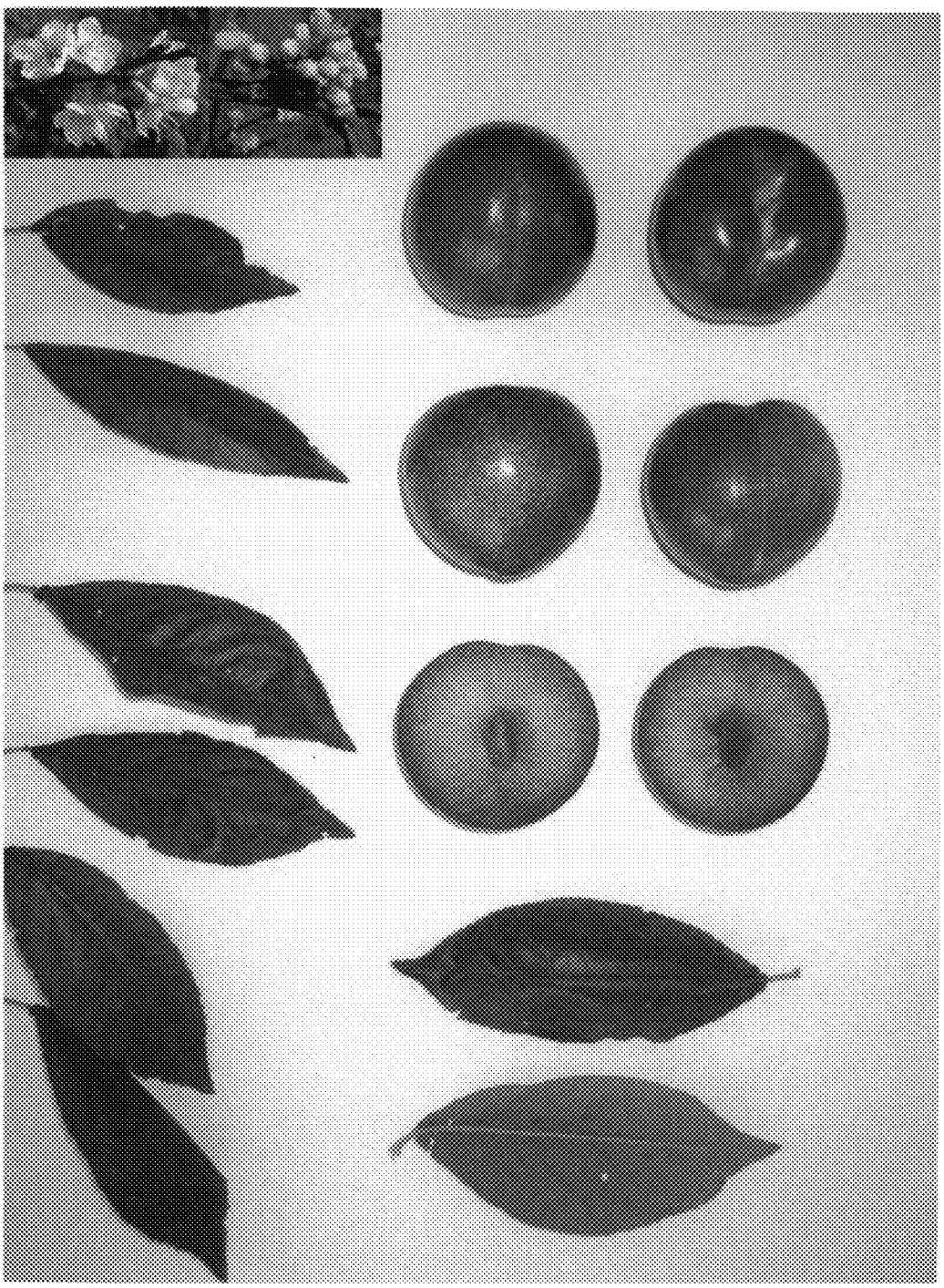

* * * * *